(12) United States Patent
Sonda et al.

(10) Patent No.: US 7,394,536 B2
(45) Date of Patent: Jul. 1, 2008

(54) METHOD AND APPARATUS FOR INSPECTING FRONT SURFACE SHAPE

(75) Inventors: Yoshiyuki Sonda, Tokyo (JP); Kimiaki Oto, Tokyo (JP); Munehisa Kato, Tokyo (JP); Atsushi Kiyama, Yamagata (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/561,517

(22) Filed: Nov. 20, 2006

(65) Prior Publication Data

US 2007/0091319 A1    Apr. 26, 2007

Related U.S. Application Data

(63) Continuation of application No. PCT/JP2005/010191, filed on Jun. 2, 2005.

(30) Foreign Application Priority Data

Jun. 4, 2004    (JP)    ............................. 2004-167621

(51) Int. Cl.
*G01N 21/00*    (2006.01)
(52) U.S. Cl. ................................. 356/239.1; 356/239.2
(58) Field of Classification Search ...................... None
See application file for complete search history.

(56) References Cited

U.S. PATENT DOCUMENTS 6,392,754 B1    5/2002    Pingel et al.

FOREIGN PATENT DOCUMENTS

| JP | 11-148813 | 6/1999 |
|---|---|---|
| JP | 2001-502800 A | 2/2001 |
| JP | 2004-514882 A | 5/2004 |

OTHER PUBLICATIONS

"Hikari Gijutsu Contact", Optical and Electrooptical Engineering Contact, published by Japan Optomechatronics Association, vol. 39, No. 2, 2001, pp. 103-110.

*Primary Examiner*—Michael P. Stafira
(74) *Attorney, Agent, or Firm*—Oblon, Spivak, McClelland, Maier & Neustadt, P.C.

(57) ABSTRACT

The present invention provides an inspection method and an inspection apparatus which can remove influence of rear surface reflection image and inspect characteristic of a front surface shape with good accuracy by an inexpensive apparatus construction. First of all, as a stripe pattern suitable for a transparent plate-shaped object 3 (object to be inspected), a stripe pattern 1 having a bright-dark pattern configured so that its reflection image produced by the front surface of the transparent plate-shaped object and its reflection image produced by a rear surface of the transparent plate-shaped object are separated in an image signal obtained by image-capturing, is determined. Thereafter, using the decided stripe pattern 1, the front surface shape of the transparent plate-shaped object 3 is evaluated by an image analysis using only a reflection image of the stripe pattern 1 produced by the transparent plate-shaped object 3.

2 Claims, 7 Drawing Sheets

S1: Preparation of stripe pattern

S2: Disposition of stripe pattern

S3: Capturing of glass plate image

S4: Analysis of captured image data

S6: Exchange of stripe pattern

S7: Decision of stripe pattern

Fig. 9

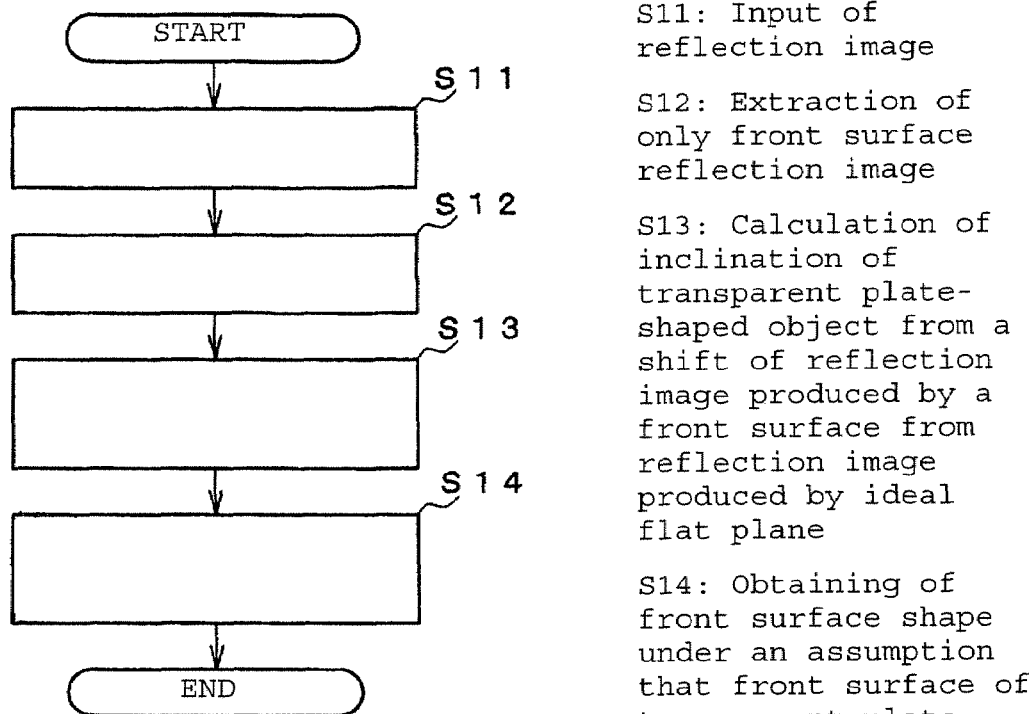

S11: Input of reflection image

S12: Extraction of only front surface reflection image

S13: Calculation of inclination of transparent plate-shaped object from a shift of reflection image produced by a front surface from reflection image produced by ideal flat plane S14: Obtaining of front surface shape under an assumption that front surface of transparent plate-shaped object is substantially flat

Fig. 10

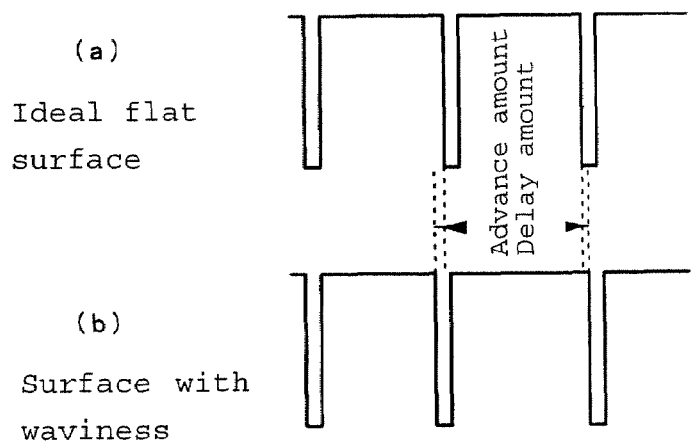

(a) Ideal flat surface (b) Surface with waviness

METHOD AND APPARATUS FOR INSPECTING FRONT SURFACE SHAPE

TECHNICAL FIELD

The present invention relates to a method and an apparatus for inspecting characteristics of surface shape such as flatness of an object typified by a glass having a mirror surface.

BACKGROUND ART

As a method for inspecting a surface shape of an object, there is a method for evaluating a surface shape of an object to be inspected, by projecting a stripe pattern having periodical bright and dark lines on the object to be inspected and measuring deviation of the bright-dark period in a reflection image produced by reflection at a front surface of the object to be inspected (for example, refer to Patent Document 1). However, when such a method is applied to a transparent plate-shaped object such as a glass plate, not only a reflection image produced by a front surface of the transparent plate-shaped object but also a reflection image produced by a rear surface of the transparent plate-shaped object are captured at the same time. From now, a reflection image from a front surface of a transparent plate-shaped object is designated as a front surface reflection image, and a reflection image from a rear surface of a transparent plate-shaped object is designated as a rear surface reflection image.

FIG. 16 is an explanation view showing that a front surface reflection image and a rear surface reflection image are formed at the same time. As shown in FIG. 16, light emitted from a point 5 on a stripe pattern is reflected by a front surface 3a of a transparent plate-shaped object 3, and focused at a capturing point 10 on a photo-receiving plane 7 of a camera through an optical path 8. Further, light transmitted through the transparent plate-shaped object 3 is reflected by a rear surface 3b of the transparent plate-shaped object 3 and focused at a capturing point 11 on the photo-receiving plane 7 through an optical path 9.

Here, depending on a period or width of the stripe pattern, there is a case that the following problems occur to a captured image signal. FIG. 17 is a wave pattern view showing an example of image signal output from a camera. FIG. 17(a) shows an image signal of front surface reflection image, and FIG. 17(b) shows an image signal of rear surface reflection image.

Further, low level indicates a level of image signal of a dark portion of the stripe pattern, and high level indicates a level of image signal of a bright portion of the stripe pattern. If the width of a dark portion of the stripe pattern is wide, the width of a low level portion in the image signal becomes wide and there is a case that a low level portion of an image signal of front surface reflection image overlaps with a low level portion of an image signal of rear surface reflection image. In this case, an image signal output from the camera becomes a signal as shown in FIG. 17(c), and inspection of front surface shape is carried out based on the signal different from the image signal (FIG. 17(a)) of front surface reflection image that is essentially required.

Further, as shown in FIG. 18, even if the width of dark portions of the stripe pattern is sufficiently narrow, if the distance T between the positions of dark portions of an image signal of front reflection image and the positions of dark portions of an image signal of rear surface reflection image, is close to an integer times of a bright-dark period of the stripe pattern, an image signal as shown in FIG. 18(c) is output from the camera. Here, FIG. 18(a) shows an image signal of front surface reflection image, and FIG. 18(b) shows an image signal of rear surface reflection image. Also in this case, inspection of surface shape is carried out based on a signal different from an image signal of front surface reflection image, which causes a problem that the surface shape cannot be inspected accurately.

As a method for solving the above problem, there are methods of weakening or removing the rear surface reflection image. For example, a method of using ultraviolet rays is one of these methods (refer to Non-Patent Document 1). Since the ultraviolet rays are absorbed in a glass, contrast of a rear surface reflection image becomes sufficiently lower than the contrast of front surface reflection image, and even if the rear reflection image overlaps with the front surface reflection image, it is possible to reduce the influence of rear surface reflection image.

Patent Document 1: JP-A-11-148813 (paragraphs 0082 to 0083 and FIG. 24)

Non-Patent Document 1: "Hikari Gijutsu Contact" (Optical and Electrooptical Engineering Contact) (published by Japan Optomechatronics Association, Vol. 39, No. 2 (year 2001), pages 103 to 110)

However, in order to realize a method of using ultraviolet rays, it is necessary to use a UV light source and to constitute a camera by special materials transmitting ultraviolet rays, which increases the cost of inspection apparatus. Further, not all wavelength of ultraviolet rays is usable for the method but it is necessary to select a wavelength region that is sufficiently absorbable into a glass in order to weaken a rear surface reflection image. There is a type of glass having a specific composition which absorbs little ultraviolet rays, for which this method can not be applied.

Under these circumstances, it is an object of the present invention to provide a method and an apparatus for inspecting front surface shape, which has an inexpensive construction, which can remove the influence of rear surface reflection image, and which can accurately inspect characteristics of front surface shape.

DISCLOSURE OF THE INVENTION

The inspection method of front surface shape of the present invention comprises projecting a stripe pattern on a transparent plate-shaped object, capturing a reflection image of the stripe pattern produced by a front surface of the transparent plate-shaped object, and inspecting the front surface shape of the transparent plate-shaped object based on an image signal obtained by the capturing, wherein the method includes a stripe pattern decision step is for deciding as the stripe pattern a stripe pattern having a bright-dark pattern configured so that its reflection image produced by the front surface of the transparent plate-shaped object and its reflection image produced by a rear surface of the transparent plate-shaped object are separated from each other in the image signal obtained by the capturing, and the method includes a front surface shape inspection step for inspecting the front surface shape of the transparent plate-shaped object by using only the reflection image of the stripe pattern produced by the front surface of the transparent plate-shaped object among reflection images contained in the image signal obtained by the capturing.

In a preferred embodiment of the inspection method of the present invention, the transparent plate-shaped object to be inspected is a glass substrate to be used for a flat display panel.

In another preferred embodiment of the inspection method of the present invention, the transparent plate-shaped object to be inspected is a blank glass plate to be used for a glass for automobiles.

In a preferred embodiment of the inspection method of the present invention, the front surface shape inspection step comprises: obtaining a shifting amount of the reflection image from an ideal reflection image captured in a case where the front surface of the transparent plate-shaped object is an ideal flat surface; obtaining inclination of the front surface shape of the transparent plate-shaped object by using the shifting amount, position information of the stripe pattern and position information of a lens center of the image capturing means; and integrating the inclination of the front surface shape under an assumption that the front surface of the transparent plate-shaped object is substantially flat, to obtain the front surface shape of the transparent plate-shaped object.

An inspection apparatus for front surface shape of the present invention is an apparatus comprising image capturing means for capturing a reflection image of a stripe pattern projected on a transparent plate-shaped object and reflected by a front surface of the transparent plate-shaped object, and the apparatus being configured to inspect the front surface shape of the transparent plate-shaped object based on an image signal captured by the image capturing means; which further comprises: as the stripe pattern, a stripe pattern having a bright-dark pattern configured so that its reflection image produced by the front surface of the transparent plate-shaped object and its reflection image produced by a rear surface of the transparent plate-shaped object are separated in the image signal captured by the image capturing means; separating means for separating the reflection image of the stripe pattern produced by the front surface of the transparent plate-shaped object from the image signal obtained by the image capturing means; and computing means for inspecting the front surface shape of the transparent plate-shaped object using the reflection image separated by the separating means.

In a preferred embodiment of the inspection apparatus of the present invention, the computing means comprises: shift amount calculation means for calculating shift amount of the reflection image from an ideal reflection image captured in a case where the front surface of the transparent plate-shaped object is an ideal flat surface; inclination calculation means for calculating inclination of the front surface shape of the transparent plate-shaped object by using the shift amount calculated by the shift amount calculation means, position information of the stripe pattern and position information of a lens center of the image capturing means; and front surface shape determining means for determining the front surface shape of the transparent plate-shaped object by integrating the inclination of the front surface shape calculated by the inclination calculation means under an assumption that the front surface of the transparent plate-shaped object is substantially flat.

BRIEF DESCRIPTION OF THE DRAWINGS

FIG. 9: A flowchart showing general flow of the second step.

FIGS. 10(a) and 10(b): Waveform views each showing an example of image signal of reflection image.

EXPLANATION OF NUMERALS

1: stripe pattern, 2: CCD camera
3: transparent plate-shaped object, 3a: front surface
3b: rear surface, 4: computer
5: point on stripe pattern, 7: photo-receiving plane
19,26: reflection image, 31,32: reflection point

BEST MODE FOR CARRYING OUT THE INVENTION

From now, an embodiment of the present invention is described with reference to drawings.

Figure 1:
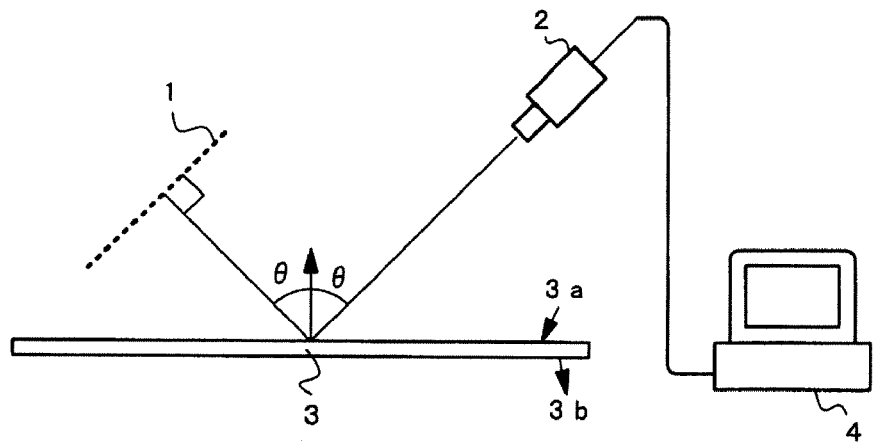
FIG. 1: A schematic view showing an outline of an inspection apparatus for inspecting flatness of front surface of a transparent plate-shaped object.
Figure 2:
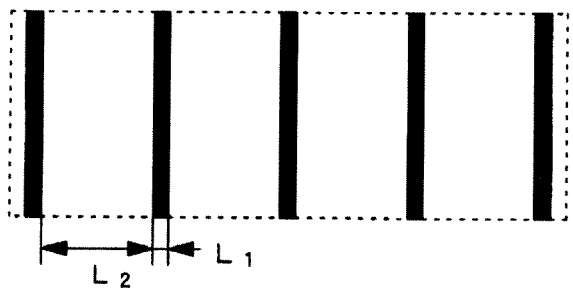
FIG. 2: An explanation view showing an example of stripe pattern.

FIG. 1 is a schematic view showing an outline of an inspection apparatus for inspecting flatness of front surface of a transparent plate-shaped object such as a glass plate. As shown in FIG. 1, the inspection apparatus is configured to capture an image of stripe pattern 1 projected on a front surface 3a of a transparent plate-shaped object 3 such as a glass plate being an object to be inspected placed on a table (not shown), by using a CCD camera 2 being image capturing means. The stripe pattern 1 is disposed on an emission plane of a light source (not shown). FIG. 2 is an explanation view showing an example of stripe pattern 1. In FIG. 2, $L_1$ indicates a width of dark portion and $L_2$ indicates a width of bright portion. $L_1+L_2$ corresponds to a bright-dark period. In a case where the stripe pattern 1 is produced by painting black portions on a transparent resin film, bright portions correspond to transparent portions and dark portions correspond to black portions.

An image captured by the CCD camera 2 is taken into a computer 4 such as a personal computer being computing means, and the computer 4 carries out image analysis. Here, the CCD camera 2 is shown in this example, but any type of camera such as an area camera, a line camera, a video camera or a still camera can be used instead of the CCD camera 2. Further, any photo-receiving apparatus capable of identifying a reflection image, such as one having arranged photosensors, may also be used.

The CCD camera 2 and the stripe pattern 1 are disposed so that the optical axis of the CCD camera 2 and a normal line to the stripe pattern 1 (specifically, a flat plane on which the stripe pattern 1 is present), are at the same angle θ to a normal line to the surface 3a of the transparent plate-shaped object 3. The angle θ is preferably 45°.

Figure 3:
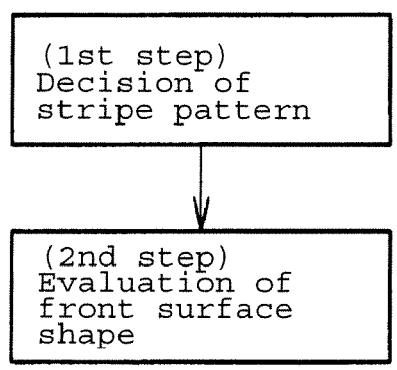
FIG. 3: A flowchart showing general flow of the inspection method for front surface shape of the present invention.

FIG. 3 is a flowchart showing general flow of the inspection method of front surface shape of the present invention. As shown in FIG. 3, in the inspection method of the present invention, as a first step, a stripe pattern decision step is conducted for deciding a stripe pattern 1 suitable for a transparent plate-shaped object 3 as an object to be inspected, and then, as a second step, using the stripe pattern 1 decided in the first step, a front surface shape inspection step is conducted for evaluating front surface shape of the transparent plate-shaped object 3 by an image analysis based on reflection image of the stripe pattern 1 produced by the transparent plate-shaped object 3. Here, in the second step, among reflection images of the stripe pattern 1 decided in the first step produced by the front surface 3a and the rear surface 3b respectively of the transparent plate-shaped objects 3, only the reflection image produced by the front surface 3a of the transparent plate-shaped object 3 is used.

Figure 4:
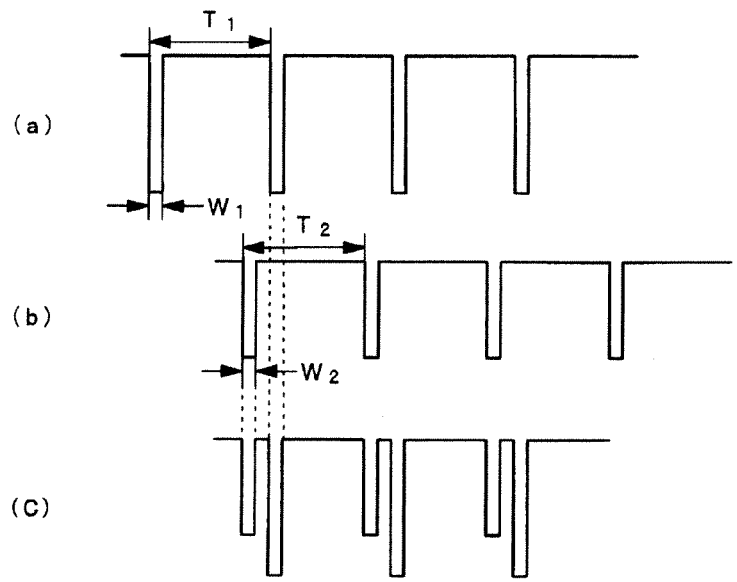
FIGS. 4(a) to 4(c): Waveform views each showing an example of output signal from a CCD camera.
Figure 17:
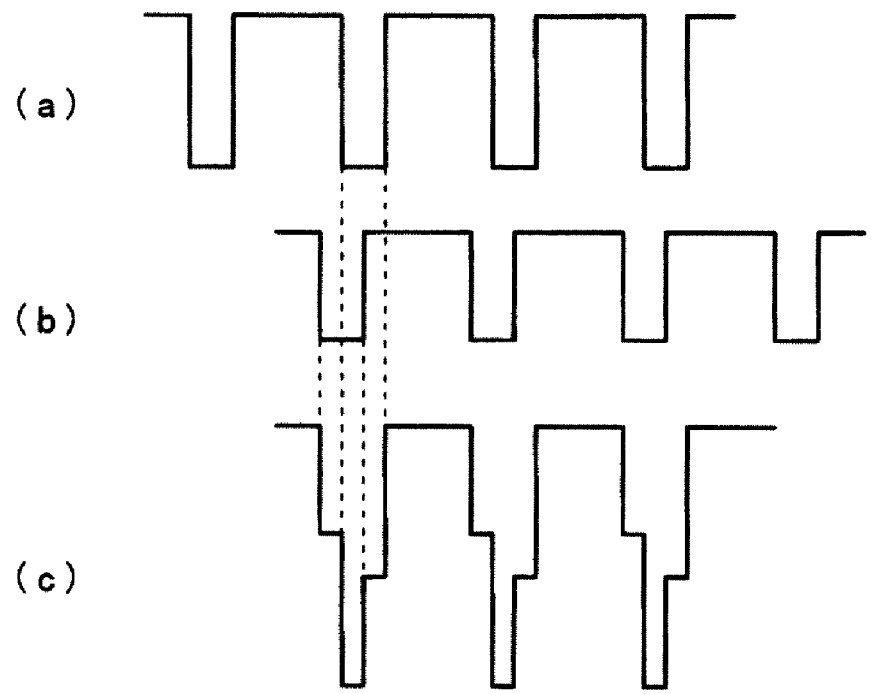
FIGS. 17(a) to 17(c): Waveform views each showing an example of image signal output from a camera.
Figure 18:
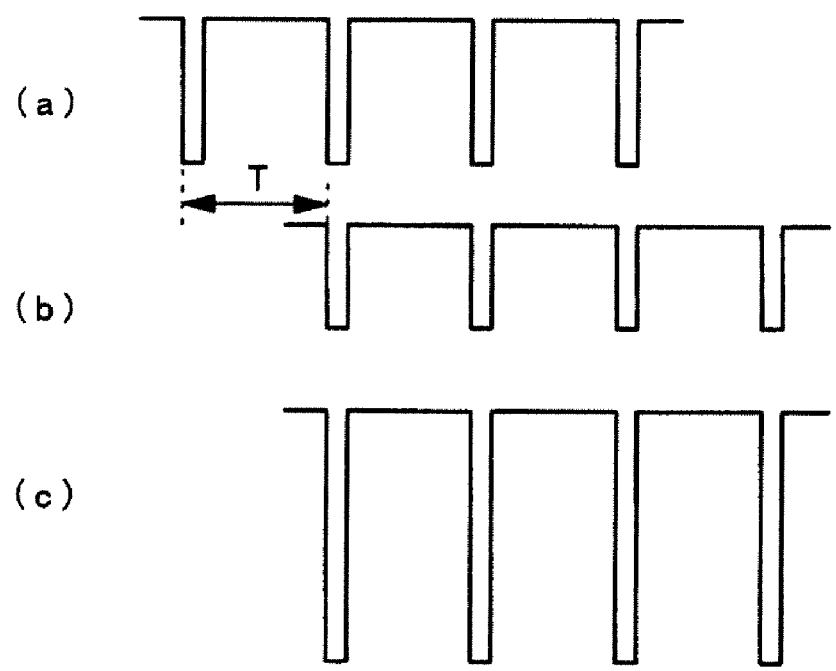
FIGS. 18(a) to 18(c): Waveform views each showing an example of image signal output from a camera.

FIG. 4(c) is a waveform view showing an example of output signal from a CCD camera 2 in a case of using a stripe pattern 1 decided in the first step. In FIG. 4, FIG. 4(a) shows an image signal of front surface reflection image, and FIG. 4(b) shows an image signal of rear surface reflection image. As shown in FIG. 4(c), the CCD camera 2 outputs a signal in which an image signal of front surface reflection image overlaps with an image signal of rear surface reflection image in the same manner as the case shown in FIGS. 17 and 18.

Here, in the present invention, the width of dark portions of the stripe pattern (corresponding to signal width $W_1$ or $W_2$) and bright-dark period (corresponding to period $T_1$ or $T_2$) are optimized so that dark portions of front surface reflection image and dark portions of rear surface reflection image do not overlap to each other in an image signal output from the CCD camera 2. Accordingly, at a time of image analysis by the computer 4, only an image signal of front surface reflection image can be easily extracted and precise front surface shape inspection can be carried out.

Figure 5:
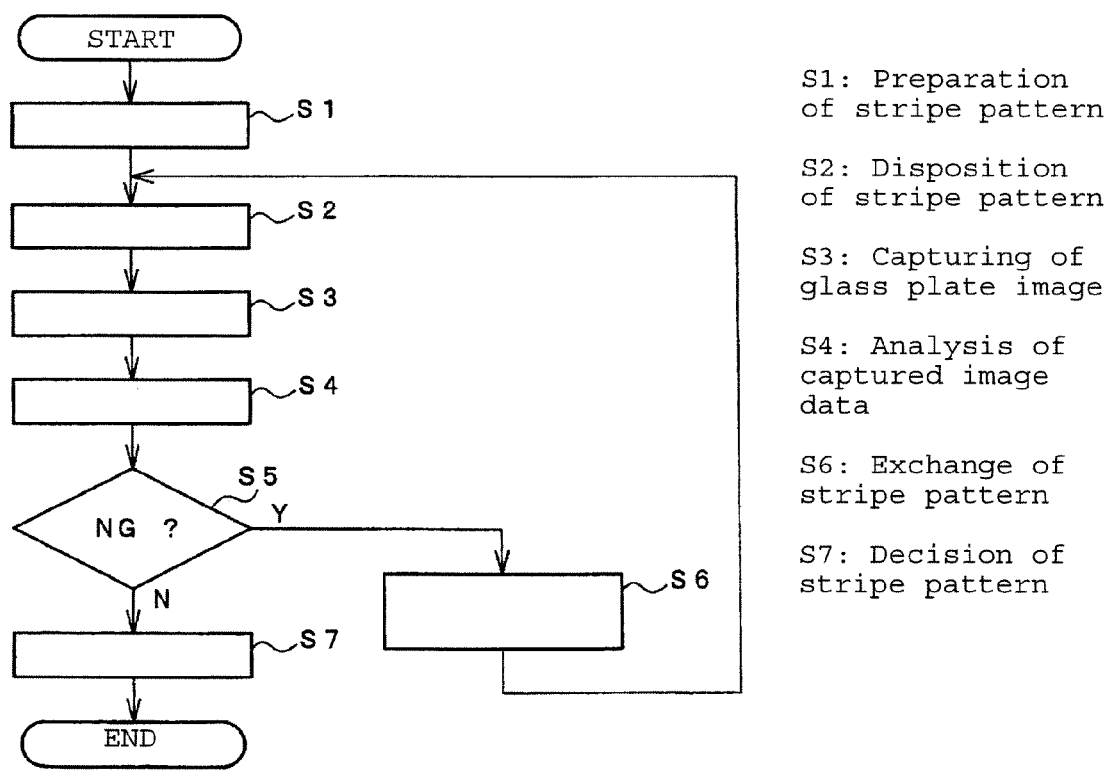
FIG. 5: A flowchart showing an example of process for deciding a stripe pattern.

Then, procedure in the first step for deciding a stripe pattern is described. FIG. 5 is a flowchart showing an example of procedure for deciding a stripe pattern. In the procedure, first of all, a plurality of stripe patterns having different printed patterns are prepared (step S1). Namely, a plurality of stripe patterns having different stripe period or stripe width are prepared. Such a stripe pattern is, for example, formed by printing a pattern on a transparent resin film by ink jet printing. Then, the stripe pattern is pasted on a light source (step S2). Then, a reflection image of the stripe pattern produced by a transparent plate-shaped object 3 is captured by a CCD camera 2 (step S3).

Then, a computer 4 inputs an image signal of the image captured by the CCD camera 2, and carries out an image analysis procedure for analyzing the image signal according to an image analysis procedure program (step S4). In the image analysis procedure, judgment is made whether or not an output signal from the CCD camera 2, namely, the image signal input from the CCD camera 2, is in a state shown in FIG. 4(c). Specifically, judgment is made whether or not the signal is in a state that signal waves corresponding to two dark portions are separated from each other. If the image signal is not in such a state (a case of NG), another stripe pattern is pasted on the light source and procedures of steps S2 and S3 are carried out again. Here, as to be described later, in a case of distinguishing a front reflection image from a rear reflection image by their amplitudes, the respective dark portions are preferably separated from each other. For example, in an image signal, a dark portion of rear reflection image is preferably positioned in the middle of two dark portions of the front reflection image.

If the computer 4 confirms that levels corresponding to two dark portions do not overlap to each other in an image signal, the stripe pattern pasted on the light source at this time is decided as a stripe pattern 1 to be used for inspecting front surface shape of a transparent plate-shaped object 3 (step S7). Thus, a stripe pattern 1 having a bright-dark pattern whose front surface reflection image and rear surface reflection image are separated in an image signal obtained by the CCD camera 2, is decided as a stripe pattern 1 suitable for inspecting front surface shape of a transparent plate-shaped object 3.

Here, in a case where the transparent plate-shaped object 3 being an object to be inspected, is a glass substrate for liquid crystal displays or for PDPs usually having a plate thickness of about 1 mm, for example, a stripe pattern as shown in an example of FIG. 2 in which the width $L_2$ of transparent portion is from about 0.9 to 1.3 mm and the width $L_1$ of black portion is from about 0.05 to 0.1 mm, is decided as a stripe pattern 1 to be used for the inspection of such a glass substrate.

Figure 6:
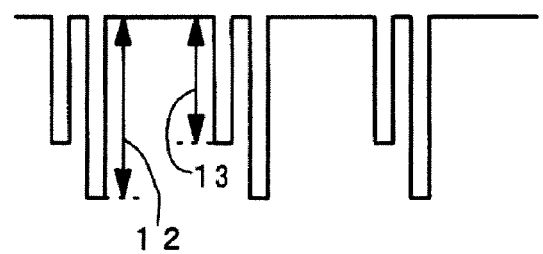
FIG. 6: A waveform view showing an output signal from a CCD camera in a case where a stripe pattern decided in the first step is used.

Then, a method for recognizing front reflection image used in the second step is described. FIG. 6 is a waveform view showing an output signal from a CCD camera 2 in a case of using a stripe pattern decided in the first step. Contrast of a stripe pattern on surfaces of a transparent plate-shaped object 3 such as a glass plate, tends to be such that contrast of front surface reflection image (corresponding to amplitude 12 in FIG. 6) is stronger than contrast of rear surface reflection image (corresponding to amplitude 13 in FIG. 6). Accordingly, it is possible to find out low level portions (low intensity portions) present periodically in a captured image signal, and to use, among these portions, portions having larger amplitudes for inspection as an image signal of front surface reflection image.

Figure 7:
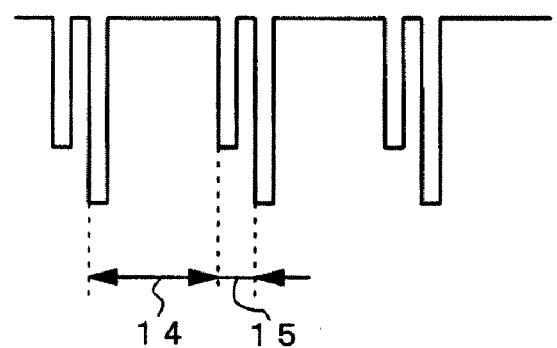
FIG. 7: A waveform view showing an output signal from a CCD camera in a case where a stripe pattern decided in the first step is used.

FIG. 7 is also a waveform view showing an output signal from CCD camera 2 in a case of using a stripe pattern decided in the first step, wherein the interval 14 shown in FIG. 7 shows an interval from a low intensity portion in an image signal of front surface reflection image to a low intensity portion in an image signal of rear surface reflection image, and an interval 15 shows an interval from a low intensity portion in the image signal of rear surface reflection image to a low intensity portion in the image signal of a front surface reflection image.

The interval 14 and the interval 15 are, in average, decided by (1) the thickness of transparent plate-shaped object 3, (2) an angle between an optical axis of CCD camera 2 and a normal line to the transparent plate-shaped object 3, and (3) bright-dark period of stripe pattern 1. By deciding the stripe pattern 1 so that the lengths of the interval 14 and the interval 15 are apparently different in the first step, it becomes easy to distinguish a front surface reflection image from a rear surface reflection image. Namely, among two low intensity portions forming the longer interval 14, one low intensity portion (for example, one present in advance side) is recognized as one produced by a front surface reflection image. Such a method of recognizing front surface reflection image is advantageous in a case where there is no large difference of contract between a front surface reflection image and a rear surface reflection image.

In the second step, image signals of both of front surface reflection image and rear surface reflection image are input from the CCD camera 2 to the computer 4, and by recognizing a front surface reflection image in the way as described above, it is possible to extract only an image signal of front surface reflection image to carry out precise surface shape inspection.

EXAMPLES

Then, an example of the first step is described. With respect to each of the glass plates being transparent plate-shaped objects 3 having the respective plate thicknesses shown in the left column of Table 1, a stripe pattern 1 with which dark portions of its front surface reflection image and dark portions of its rear surface reflection image do not overlap, is decided by an experiment. Table 1 shows that, for example, a stripe pattern having a bright-dark period (pitch) of 0.9 mm, 1.1 mm or 1.3 mm can be used as a stripe pattern 1 suitable for inspecting surface shape of the transparent plate-shaped object 3 having a plate thickness of 0.35 mm. The width of dark portions is 50 μm or 100 μm in each case.

TABLE 1

| Plate thickness (mm) | Pitch of stripe pattern (mm) |
| --- | --- |
| 0.35 | 0.9, 1.1, 1.3 |
| 0.4 | 0.9, 1.1, 1.3 |
| 0.55 | 0.9, 1.1, 1.3 |
| 0.7 | 1.1, 1.3 |
| 0.85 | 1.1, 1.3 |
| 1.1 | 1.3 |
| 1.25 | 1.3 |
| 1.6 | 0.8, 0.9 |
| 2.0 | 1.1 |
| 2.1 | 1.1 |
| 2.3 | 1.3 |
| 3.0 | 1.3 |
| 5.0 | 1.1, 1.3 |
| 6.0 | 1.3 |

Figure 8:
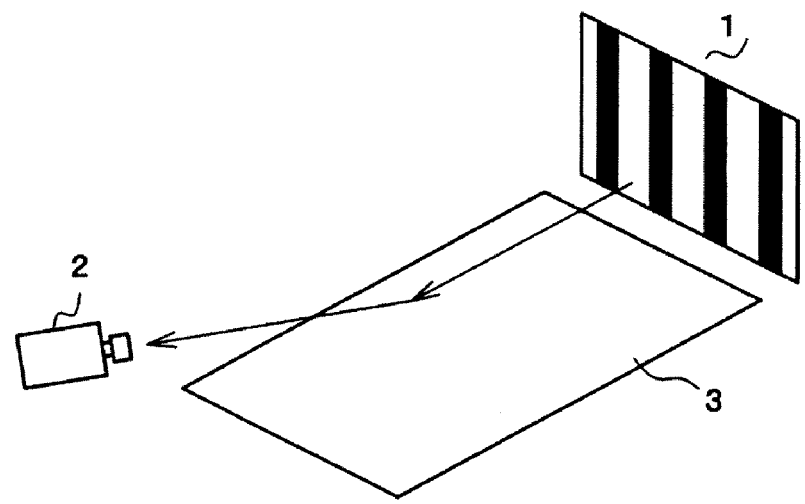
FIG. 8: An explanation view showing a front surface shape inspection being carried out.

Then, a specific example of front surface shape inspection method in the second step is described. FIG. 8 5 is an explanation view showing an example of front surface shape inspection using a stripe pattern 1. As the stripe pattern 1, one decided in the step 1 is disposed. Namely, a stripe pattern 1 is used, which has a bright-dark pattern whose image signals captured by a CCD camera 2 are 10 separated. Here, in FIG. 8, positions of the stripe pattern 1 and the CCD camera 2 are schematically shown, but positional relationship of the stripe pattern 1 and the CCD camera 2 with respect to a transparent plate-shaped object 3, is the same as the positional relationship in the first step. Further, light reflected 5 by entire front surface of the transparent plate-shaped object 3, reaches an image-capturing plane of the CCD camera 2 at the same time.

FIG. 9 is a flowchart showing an outline of the process of second step. As shown in FIG. 9, at a time of front surface shape inspection, at first, a computer 4 (not shown in FIG. 8) inputs an image signal of an image captured by the CCD camera 2 (step S11). Namely, the computer 4 inputs an image signal of a reflection image of the stripe pattern 1 produced by the transparent plate-shaped object 3. When there is waviness (undulation, distortion) on a front surface of the transparent plate-shaped object 3, position of a low intensity portion in the image signal of the reflection image captured by the CCD camera 2, shifts from a position of the low intensity portion in an image signal produced by an ideal plane having no waviness. Namely, the position of low intensity portion produced by the transparent plate-shaped object 3 advances or retreats from the position of low intensity portion in an image signal of the reflection image produced by the ideal plane.

Then, the computer 4 extracts only an image signal of front surface reflection image from the image signal captured by the CCD camera 2 by the above-mentioned method (refer to FIG. 6 and FIG. 7) (step S12). Namely, the computer 4 finds low intensity portions periodically appear in the image signal obtained by the CCD camera 2, recognizes low intensity portions having larger amplitudes among such low intensity portions as image signals of front surface reflection image (refer to FIG. 6), or the computer 4 recognizes among two low intensity portions constituting longer interval 14 (refer to FIG. 7) in the image signal obtained by the CCD camera 2, one low intensity portion (e.g. one ahead of the other one) as a low intensity portion produced by the front surface reflection image, so as to extract only an image signal of front surface reflection image. Accordingly, the computer 4 also plays a role of separating means for carrying out a process of separating a front surface reflection image of the transparent plate-shaped object 3 from the image signal obtained by the CCD camera 2. In the following explanation, an "image signal of reflection image" means an image signal of front surface reflection image separated from an image signal obtained by the CCD camera 2. Further, to simplify the explanation, each low intensity portion in the image signal of reflection image may be simply referred to as reflection image in this document.

The computer 4 calculates inclination (differential value) of surface shape of front surface of the transparent plate-shaped object 3 by a front surface shape inspection program according to a position shift (advance information or retreat information) of an obtained front surface reflection image with respect to a position of reflection image produced by an ideal plane (step S13). Further, the computer 4 obtains a surface shape by carrying out an integration calculation under an assumption that the front surface of the transparent plate-shaped object 3 is substantially flat (step S14).

FIGS. 10(*a*) and 10(*b*) are each an waveform view showing example of image signal of reflection image. FIG. 10 only shows an image signal of front surface reflection image. As shown in FIG. 10(*b*), low intensity portions of a reflection image produced by a plane having waviness advances or retreats spatially with respect to low intensity portions of a reflection image (shown in FIG. 10(*a*)) produced by an ideal plane having no waviness on the surface.

Figure 11:
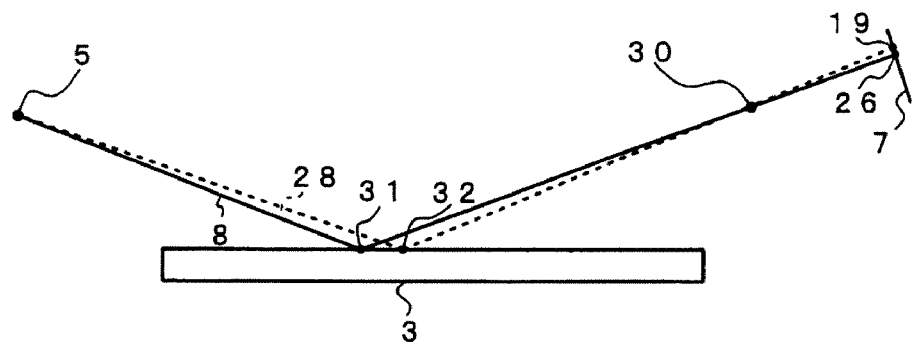
FIG. 11: An explanation view showing an example in which a path of observed reflection image advances from a reflection image produced by an ideal flat plane.
Figure 12:
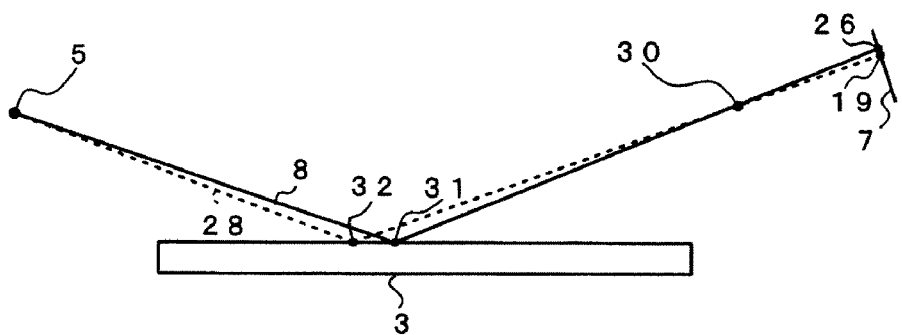
FIG. 12: An explanation view showing an example in which a path of observed reflection image retreats from a reflection image produced by an ideal flat plane.

With reference to explanation views of FIG. 11 to FIG. 15, inspection method of front surface shape is described in detail. As described above, in a case where waviness is present on a front surface of a transparent plate-shaped object 3, position of an obtained reflection image advances or retreats with respect to a position of reflection image formed with light reflected by an ideal surface. FIG. 11 is an explanation view showing a state that a reflection image 26 advances with respect to a reflection image 19 produced by an ideal plane. Further, FIG. 12 is an explanation view showing a state that the reflection image 26 retreats with respect to the reflection image 19 produced by the ideal plane. In each of FIG. 11 and FIG. 12, a path 8 shown by a solid line shows an actual optical path. Light emitted from a point 5 on a stripe pattern 1 is reflected at a reflection point 31 on a surface of a transparent plate-shaped object 3, passes through a lens center 30 and reaches a photo-receiving plane 7 of a CCD camera 2 to form a reflection image 26.

A path 28 shown by a dashed line indicates an optical path in a case where the front surface of the transparent plate-shaped object is an ideal plane, in which light is emitted from the point 5 is reflected at a reflection point 32 on a front surface of a transparent plate-shaped object 3, passes through a lens center 30 of the CCD camera 2 and reaches a photo-receiving plane 7 of a photo-receiving element (CCD). In this case, reflection image 19 shown in FIG. 11 or FIG. 12 is formed on the photo-receiving plane 7. Here, the reflection image 19 is an image formed under an assumption that the glass surface is an ideal plane, and is not a really formed image.

In the computer 4, the position of reflection image formed with light reflected by an ideal surface is memorized as a position of ideal reflection image in advance. A bright-dark pitch (period) in a stripe pattern 1 is known. Further, positional relationship of the stripe pattern 1 and the CCD camera 2 with respect to the transparent plate-shaped object 3 is also known. Accordingly, from these known information, it is possible to determine a position of reflection image 19 formed by light reflected by the ideal surface. Here, the position of reflection image 19 formed by light reflected by the ideal surface, may be determined based on a direct image of the stripe pattern 1 captured and output as a signal by the CCD camera 2. Based on the position of the reflection image 19 formed by light reflected by the ideal surface, the computer 4 can obtain information of a shift amount (advance amount or retreat amount) of the position of really obtained reflection image 26 from the reflection image 19.

Figure 13:
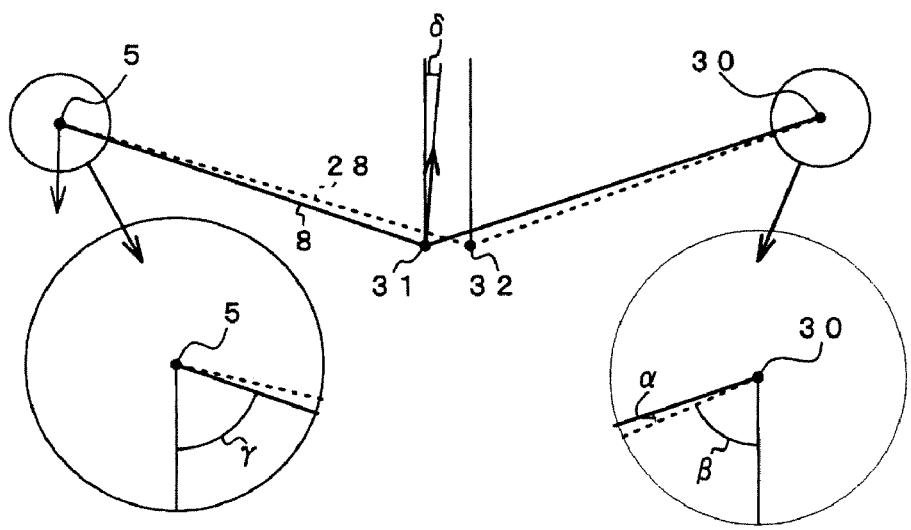
FIG. 13: An explanation view showing the relation between the degree of advance and inclination of curved shape in a case where a path of an observed reflection image advances from a reflection image produced by an ideal flat plane.

FIG. 13 is an explanation view showing the relation between the degree of advance and inclination (differential value) of surface shape in a case where a reflection image 26 advances from a reflection image 19 produced by an ideal surface. Further, FIG. 14 is an explanation view showing the relation between the degree of delay and inclination (differential value) of a surface shape in a case where the reflection image 26 retreats from the reflection image 19 produced by an ideal plane.

Figure 14:
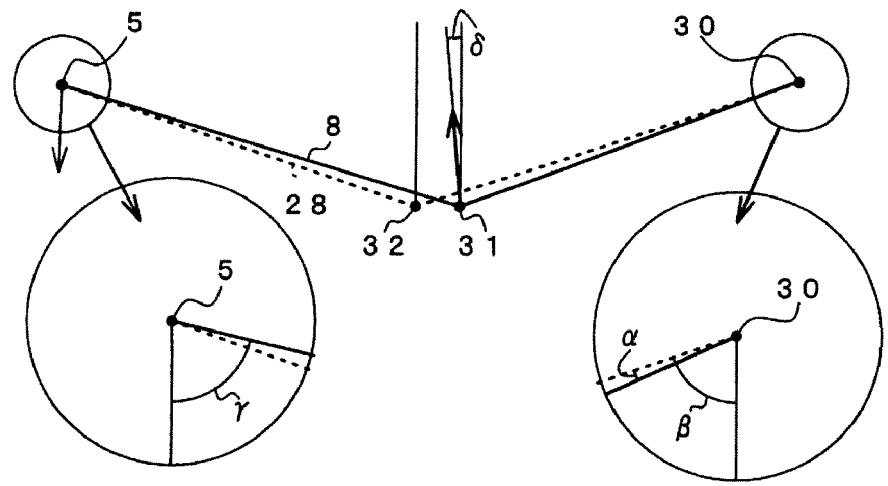
FIG. 14: An explanation view showing the relation between the degree of advance and inclination of curved shape in a case where a path of an observed reflection image retreats from a reflection image produced by an ideal flat plane.

In each of FIG. 13 and FIG. 14, α indicates an angle of a vector extending from the lens center 30 towards the path 8 with respect to a vector extending from the lens center towards the path 28. β indicates an angle of a vector extending in vertically downward direction from the lens center 30 with respect to a vector extending from the lens center 30 towards the path 28. γ indicates an angle of a vector extending from the point 5 towards the path 8 with respect to a vector extending in vertically downward direction from the point 5. Further, δ indicates an angle of a normal vector to a waviness surface at a reflection point 31, with respect to a vertically upright vector at the reflection point 31 (in other words, δ indicates inclination of the normal vector). Here, a waviness surface means a portion of a surface 3a of a transparent plate-shaped object 3 where waviness is present.

Each of these angles takes positive value when the direction inclines in a counter clockwise direction from the reference vector. Accordingly, in a state shown in FIG. 13, α<0 and δ<0, and in a state shown in FIG. 14, α>0 and δ>0.

Formula 1:

$$\delta = \frac{\alpha - \beta + \gamma}{2} \quad (1)$$

Figure 15:
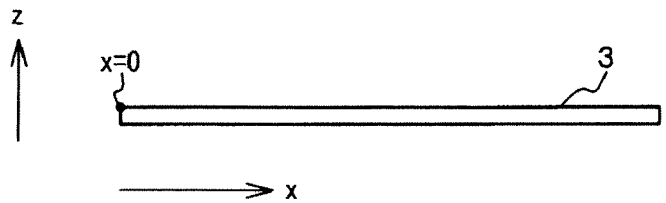
FIG. 15: An explanation view showing definitions of x axis and z axis.
Figure 16:
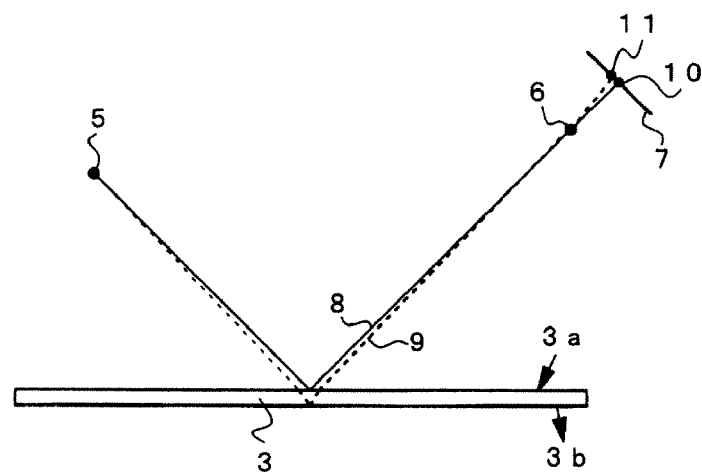
FIG. 16: An explanation view showing an example in which a front refection image and a rear reflection image are formed at the same time.

The inclination δ of the normal vector is represented by Formula (1). Provided that the front surface shape is represented by a function z=f(x), an inclination (differential value)=tan δ of front surface shape, is represented by Formula (2). x axis and z axis are directions as shown in FIG. 15, and a point of x=0 is, for example, defined as a left end point of the front surface of the transparent plate-shaped object 3.

Formula 2:

$$f'(x) = \frac{df(x)}{dx} = \tan\delta \quad (2)$$

Accordingly, the surface shape z is represented by Formula (3), in Formula (3), C is an integration constant. The front surface shape of a transparent plate-shaped object 3 employed for a flat panel display such as a liquid crystal display or a PDP, is substantially flat that may contain fine waviness. Accordingly, the relation shown in Formula (4) is considered to be satisfied. Namely, a condition is applied, according to which an average value of waviness on the front surface of the transparent plate-shaped object 3, is zero. Accordingly, the integration constant C in Formula (3) is determined so as to satisfy the assumption of Formula (4). Here, in Formula (4), the ideal surface is defined as a plane of z=0.

Formula (3):

$$z = \int f'(x)dx + C \quad (3)$$

Formula (4):

$$\int f(x)dx = O \quad (4)$$

Specifically, the following procedures are carried out.

The computer 4 inputs reflection images 26 from the CCD camera 2, to obtain positional information of each reflection image 26 on a two-dimensional plane (specifically, positional information of each of low-intensity portions). Further, the computer 4 can also recognize positional information of each reflection image 19 produced by an ideal plane (specifically, positional information of each of low-intensity portions). The positions of reflection images 26 and 19 on a photo-receiving plane 7, correspond to the positions of reflection points 31 and 32 on the surface of the transparent plate-shaped object 3.

Further, the position of lens center 30 is fixed and the computer can recognize the position of point 5 in the stripe pattern 1, namely, the positional information of the stripe pattern 1. In the computer 4, a position information of lens center showing the position of the lens center 30, and the position information of stripe pattern 1 showing the position of point 5 in the stripe pattern 1, are memorized in advance. Here, the position of point 5 in the stripe pattern 1 does not mean a specific position but means each position in the stripe pattern 1 corresponding to each reflection image 26 or 19 (specifically, each low intensity portion). Since the positions of reflection points 31 and 32 can be determined from the positions of the reflection images 26 and 19 in the photo-receiving plane 7, and since the position of lens center 30 is known, the computer 4 can calculate each of the angles α, β and γ of each reflection image 26. Accordingly, δ of each reflection image 26 can be calculated based on formula (1). Here, the position of reflection point 31 corresponding each reflection image 26 is designated by an x value in Formulae (2) to (4).

Since δ of each reflection image 26 is calculated, the computer 4 can easily calculate a value of tan δ(=f' (x)) of each reflection image 26. Assuming that n pieces of f' (x), that are f' ($x_1$), f' ($x_2$), f' ($x_3$), . . . , f' ($x_n$), are obtained with respect to each reflection image 26, Δ(x) is defined as follows.

$$\Delta(x_1)=(f'(x_1)+f'(x_2))\times(x_2-x_1)/2$$

$$\Delta(x_2)=(f'(x_2)+f'(x_3))\times(x_3-x_2)/2$$

$$\Delta(x_{(n-1)})=(f'(x_{(n-1)})+f'(x_n))\times(x_n-x_{(n-1)})/2$$

The front surface shape can be calculated by carrying out numerical integration of f' (x). Specifically, the computer 4 obtains the height of waviness at each x by calculating:

$$f(x_n)=\Delta(x_1)+\Delta(x_2)+\ldots+\Delta(x_{(n-1)})$$

The front surface shape thus obtained does not always satisfy Formula (4), but the computer 4 can obtain a front surface shape satisfying Formula (4) by setting the integration constant C in Formula (3) as follows:

$$C = -(f(x_1) + f(x_2))\times(x_2 - x_1)/2$$
$$-(f(x_2) + f(x_3))\times(x_3 - x_2)/2$$
$$\ldots$$
$$-(f(x_{(n-1)}) + f(x_n))\times(x_n - x_{(n-1)})/2$$

Front surface shape can be measured by the above method. In the method, since an appropriate stripe pattern is decided in the first step, it is possible to obtain a front surface shape without being affected by a rear surface reflection image. As a result, it is possible to inspect characteristics of front surface shape with good accuracy. Here, at a time of evaluating e.g. a flatness of a front surface of a transparent plate-shaped object 3 based on the front surface shape thus obtained, the evaluation may carried out by an inspector, or by the computer 4 in such a way that the computer 4 memorizes a reference value of good product in advance and output the comparison result with the reference value. Further, in the inspection method of front surface shape of the present invention, since only addition and subtraction operations are required for obtaining angles from measurement values and for integration, calculation volume of the computer 4 is not so large.

Here, the computer 4 serves as: shift amount calculation means for calculating shift amount of reflection image with respect to an ideal reflection image captured in a case where the front surface of the transparent plate-shaped object 3 is an ideal flat, inclination calculation means for calculating inclination of the front surface shape of the transparent plate-shaped object 3 using the shift amounts, position information of the stripe pattern 1 and position information of the lens center of the CCD camera 2, and front surface shape determining means for obtaining a front surface shape of the transparent plate-shaped object 3 by integrating the inclination of the front surface shape under an assumption that the front surface of the transparent plate-shaped object 3 is substantially flat.

Further, in the above embodiment, a glass plate to be employed for a flat panel display such as liquid crystal display or PDP, is assumed as the transparent plate-shaped object 3, but the present invention can be applied also to a transparent plate-shaped object such as a glass substrate (blank plate) or resin plate to be used for e.g. automobiles, ships, airplanes or buildings.

INDUSTRIAL APPLICABILITY

According to the present invention, a stripe pattern is decided so that only a reflection image produced by front surface of a transparent plate-shaped object can be extracted from an image signal obtained by image capturing means, and thus, it is possible to remove influence of rear surface reflection image and to inspect characteristic of front surface shape with good accuracy by an inexpensive apparatus construction.

The present invention is suitably applied to inspection of front surface flatness of a transparent plate-shaped object.

The entire disclosure of Japanese Patent Application No. 2004-167621 filed on Jun. 4, 2004 including specification, claims, drawings and summary is incorporated herein by reference in its entirety.

What is claimed is:

1. A method for inspecting a front surface shape, comprising: projecting a stripe pattern of light and dark segments on a transparent plate-shaped object;
   capturing a reflection image of the stripe pattern produced by a front surface and a rear surface of the transparent plate-shaped object with a camera;
   determining whether a signal wave corresponding to the reflection image captured by the camera is in a state that a first signal wave portion corresponding to a first dark portion of the stripe pattern reflected from the front surface and a second signal wave portion corresponding to a second dark portion of the stripe pattern reflected from the rear surface are separated from each other and do not coincide;
   analyzing the signal wave corresponding to the reflection image captured by the camera to recognize a signal wave that corresponds to an image reflected from the front surface, wherein the first signal wave portion is determined by comparing magnitudes of the first and second signal wave portions to determine lowest intensity portions as the first signal wave portions, the lowest intensity portions corresponding to the image reflected only by the front surface; and
   using the first signal wave portions which correspond to the image reflected only by the front surface to inspect the front surface shape.

2. The method of claim 1, further comprising:
   selecting the stripe pattern so that a length of a first interval between a first low intensity portion in the image signal of a front surface reflection image to a second low intensity portion in the image signal of a rear surface reflection image adjacent to the first low intensity portion is different than a second interval between the second low intensity portion in the image signal of the rear surface reflection image to another first low intensity portion in the image signal of a front surface reflection image adjacent to the second low intensity portion.

* * * * *